United States Patent [19]

Agarwal et al.

[11] Patent Number: 4,935,118

[45] Date of Patent: Jun. 19, 1990

[54] SELF HEATED SENSOR PACKAGE

[75] Inventors: Anil K. Agarwal, Camarillo, Calif.; Joseph N. Panzarino, Northboro; Malcolm E. Washburn, Princeton, both of Mass.

[73] Assignee: Norton Company, Worcester, Mass.

[21] Appl. No.: 842,453

[22] Filed: Mar. 21, 1986

Related U.S. Application Data

[63] Continuation-in-part of Ser. No. 818,056, Jan. 10, 1986, abandoned, which is a continuation of Ser. No. 717,054, Mar. 28, 1985, abandoned.

[51] Int. Cl.[5] ............................................. G01N 27/46
[52] U.S. Cl. ..................................... 204/421; 204/424; 219/553
[58] Field of Search .................. 204/1 S, 421–429; 219/270, 553

[56] References Cited

U.S. PATENT DOCUMENTS

| 3,576,730 | 4/1971 | Spacil ................... 204/427 |
| 3,597,345 | 8/1971 | Hickam et al. ......... 204/427 |
| 3,598,711 | 8/1971 | Flais ....................... 204/427 |
| 3,875,476 | 4/1975 | Crandall et al. ....... 219/553 |
| 3,875,477 | 4/1975 | Fredriksson et al. .. 219/270 |
| 4,098,650 | 7/1978 | Sayles .................... 204/427 |
| 4,327,122 | 4/1982 | Chakupurakal ........ 204/427 |
| 4,503,319 | 3/1985 | Moritoki et al. ....... 219/553 |

FOREIGN PATENT DOCUMENTS 2351815 4/1975 Fed. Rep. of Germany ...... 204/428

Primary Examiner—T. Tung
Attorney, Agent, or Firm—Arthur A. Loiselle, Jr.

[57] ABSTRACT

An oxygen sensing package includes a solid electrolyte sensor and a silicon carbide heating element arranged so as to surround the solid electrolyte and radiate heat to it from convex surfaces.

4 Claims, 1 Drawing Sheet

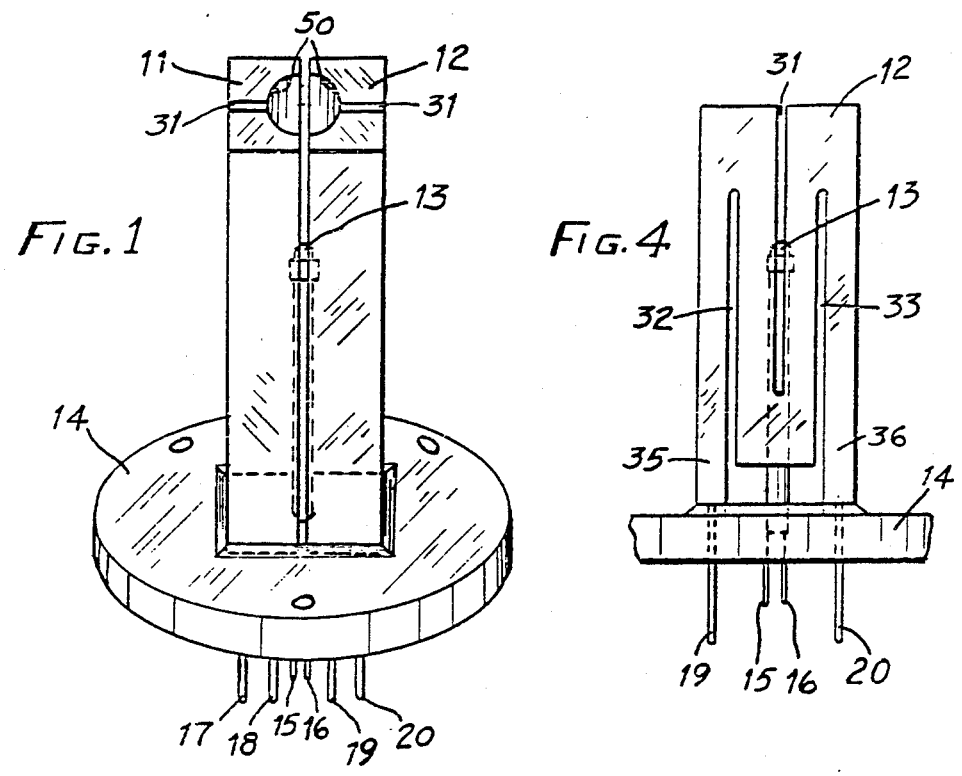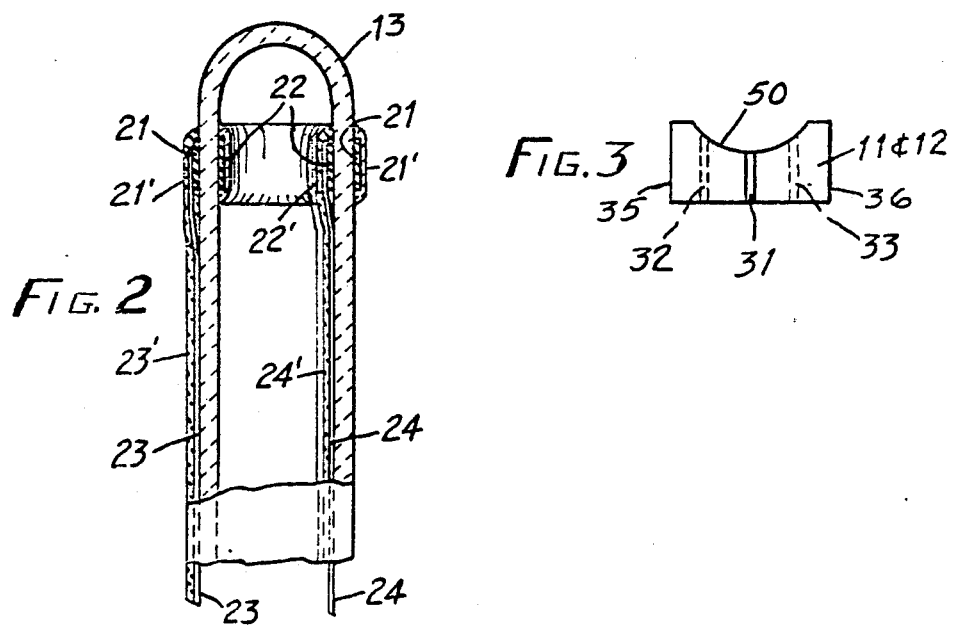

SELF HEATED SENSOR PACKAGEn

BACKGROUND OF THE INVENTION

This application is a continuation-in-part of U.S. Application Ser. No. 06/818,056, filed Jan. 10, 1986, now abandoned, which was a continuation of U.S. Application Ser. No. 06/717,054 filed Mar. 28, 1985 now abandoned.

Zirconia stabilized with $Y_2O_3$, CaO, MgO, etc. is widely used for oxygen sensors in a variety of industrial and automotive applications. Stabilized zirconia, being a solid state oxygen ion conductor preferentially transports oxygen ions from a gas stream having a higher oxygen partial pressure to a gas stream having a lower oxygen partial pressure, if the two gas streams are isolated, of course. The transport rate (response time) is governed by the operating temperature. The E.M.F. of this oxygen cell is given by the following Nernst Equation:

$$E = \frac{RT}{NF} \ln \frac{PO_2\,(I)}{PO_2\,(II)}$$

where R is gas constant, T is temperature in °K, N is charge, F is the Faraday constant, $PO_2(I)$ and $PO_2(II)$ are oxygen partial pressure in the two sides respectively. Several models are commercially available today. They all can be classified in two following categories:

(1) In situ type
(2) Sampling Type

In the in situ type the sensor is placed into the furnace and senses the atmospheric oxygen. The sensor is heated by the furnace heat or, if insufficient, by external platinum or nichrome heaters wrapped around it to provide the temperature for adequate operation. The heating elements have to be protected from the furnace atmosphere which adds complexity and weight. The complexity of the in situ sensors is avoided by a sampling type of device wherein a probe is inserted into the furnace or other atmosphere to be measured and a sample is drawn out which is then passed through an external sensor maintained in at desired temperature. This type of device is also useful as a portable unit. However, the problem of condensation of the gases through the line from the furnace to be meansured to the sensor unit comes into play. One has to heat the line to prevent condensation and also worry about the calibration of the sensor to the operating temperature of the furnace rather than of the sensor to obtain the correct $PO_2$. Looking at the above situation, there exists a need for an efficient in situ device with an inert heating element which is stable against atmosphere and temperature and also is inexpensive for real time atmosphere monitoring. Some of the applications for such a device are in diffusion furnaces, gas analysis, sintering and brazing furnaces, glass melting, combustion and heat treatment furnaces, nitriding furnaces, etc.

BRIEF SUMMARY OF THE INVENTION

An in situ oxygen sensing apparatus accomplishing the objectives of the invention is provided by the use of a ceramic (preferably silicon carbide) resistance heating element surrounding the solid electrolyte and heating the electrolyte sensor by radiation and convection.

IN THE DRAWINGS

FIG. 1 is a perspective view of a sensor of the invention.
FIG. 2 is a cross sectional view of the sensor element.
FIG. 3 is a top view of one of the heating elements.
FIG. 4 is a side view of a heating element.

DETAILED DESCRIPTION OF THE INVENTION

Silicon carbide igniters have been commercially gases and operate successfully in the typical atmospheres as mentioned above. These igniters have survived the most stringent requirement of thermal and gas cycling for extended periods of time. So much so that they have been accepted by the home appliance market. Needless to say these markets are very conservative in product selection because of reliability and cost consciousness. Typical igniters are described in U.S. Pat. No. 3,875,477, the disclosure of which is incorporated herein by reference.

A working unit which uses two planoconcave SiC heating elements, 11, 12, surrounding $ZrO_2$ 13 sensor tube is shown in FIG. 1. This whole assembly is mounted on an insulating ceramic disk 14 which butts against a furnace port and seals the furnace atmosphere completely. The electronics is controlled from a separate unit which processes the E.M.F. from connectors 15, 16, and correlates that to the oxygen partial pressure in the furnace. The heaters are powered through connectors 17, 18, 19, and 20.

FIG. 2 shows in more detail a longitudinal cross section through the sensor element 13 and associated annular electrodes 21 and 22, with leads 23 and 24 to the connections in the base 14. The leads may be protected by a flame sprayed coating 23' and 24'. Similarly, porous electrodes 21 and 22 may be protected by a plasma or flame sprayed coating 21', 22', of a material of the same composition as the solid electrolyte, or a porous coating of a refractory material such as cordierite or spinel.

The connectors from the electrodes may be connected to a high impedance voltmeter or the other measuring and control devices, not part of the present invention, but well known in the art.

FIG. 3 shows a top view of one of the heating elements 11 or 12, and FIG. 4 shows a left side view of the heating element of FIG. 3. The element is provided with slots 31, 32, and 33, so arranged that the element effectively has outer legs 35 and 36 which function as opposite electrical ends of a conductor, whereby a voltage drop applied across the ends 35 and 36 produces a heating current in the silicon carbide body. The surface directed toward the sensor 13 is shown as parabolic at 50 in FIG. 3 to direct the heat on to the sensor with maximum efficiency. Other concave shapes such as circular may be used.

While the preferred sensor solid electrolyte is doped zirconia, the particular chemistry of the sensor is not part of this invention and the sensor may be made of any suitable material which can conduct oxygen ions and produce a voltage across its electrodes in response to an oxygen partial pressure differential.

Referring to the drawing, it should be noted that the geometry of the heating elements of the heater is such that the most resistant (smallest conductive cross section) of the heater is interior of the sides and ends of the elements. Thus the highest temperature is directed at the sensor. Such control of the heating location, by adjusting the geometry of the unit, is possible because of the use of conductive ceramic material in the heater having a relatively high resistivity as compared to metallic conductor resistance heating elements. In cases where battery power is used or the power supply is limited, the increased efficiency of the heater produced by the illustrated geometry is an added benefit.

When the heater surrounds the outside of the sensor, as in FIGS. 2 and 3 of the drawing, a chamber is formed around the sensor which acts as a buffer to prevent immediate direct access of the ambient gas outside the heater. In addition, since gas accessing the space between the heater and the sensor must flow close to the hot surfaces of the heating element, excess oxygen will tend to react with any uncombusted products, thereby insuring an equilibrium oxygen partial pressure condition for the sensed gas. In addition the buffer chamber formed by the heater protects the sensor against fouling by solid combustion products.

Conventionally prepared SiC heating elements have been found to be inoperative in that false readings of oxygen content are obtained after 3 to 6 months of use. This is apparently caused by slow oxidation of free silicon or free carbon in the elements. While simple heating of the elements in an oxidizing atmosphere at 1200° C. for 10 to 15 hours avoids this problem, added protection of the elements can be achieved by filling the surface pores of the SiC heaters with fine ceramic powder such as $Si_3N_4$; and heating to oxidize any materials which would interfere with the accuracy. The $Si_3N_4$ is preferably applied in the form of a slurry.

In a comparison test of an atmosphere at a pressure of one atmosphere containing an oxygen partial pressure of about $10^{-4}$ atmospheres of oxygen, an untreated SiC heater and a ceramic coated but unvented heater both gave erroneous readings of the oxygen partial pressure as $10^{-16}$ atmosphere. When an SiC element which had been treated at 1200° C. for 10 to 15 hours was employed, the correct pressure of $10^{-4}$ atmosphere was obtained, as was the case when the sensor was employed in a temperature controlled atmosphere with no SiC element. Thus, treatment of the SiC to remove all materials oxidizable at the temperature range involved (around 700° C.) and/or treatment to prevent access of the oxidizeable material to the atmosphere being tested is required.

For added protection of the heating element against oxidation, the pores may be filled with a mixture of fine silicon carbide and sodium silicate, fired to a glassy dry state. Other pore filling material such as fine silicon nitride may also be used as taught in U.S. Pat. No. 4,187,344.

Another type of ceramic heating element would be that described in copending U.S. patent application Ser. No. 669,399 filed Nov. 11, 1984, in which structures with controlled electrical characteristics are created with mixtures of aluminum nitride, molybdenum disilicide, and silicon carbide. In accordance with the teachings of that patent specification, silicon nitride or boron nitride may be used as the nitride phase. U.S. Pat. Nos. 3,890,250; 3,649,310; and 3,875,476 also disclose ceramic heating elements.

What is claimed is:

1. A device for measuring the oxygen partial pressure in gases comprising a solid electrolyte element having an inside and an outside and having one end closed, one side of which is exposed to a reference pressure of oxygen, the other side of which is exposed to the oxygen partial pressure to be measured, a heating element spaced from and surrounding one side of said solid electrolyte so as to form a chamber, said heating element being ceramic, heated by electrical resistance, and including heat radiating surfaces spaced from and concentric with said solid electrolyte element, said heating element being free of oxidizable material.

2. A device as in claim 1 in which the heating element is composed of at least two parts having concave inner radiating surfaces, and having a central concentrated heat zone.

3. A device as in claim 1 in which the heating element is mounted in one end in a non-conducting ceramic base.

4. A device as in claim 1 in which the said ceramic heating element is composed of a material selected from the group consisting of silicon carbide, silicon nitride, molybdenum disilicide and mixtures thereof.

* * * * *

UNITED STATES PATENT AND TRADEMARK OFFICE
CERTIFICATE OF CORRECTION

PATENT NO. : 4,935,118
DATED : June 19, 1990
INVENTOR(S) : Anil K. Agarwal, Joseph N. Panzarino and Malcolm E. Washburn It is certified that error appears in the above—identified patent and that said Letters Patent is hereby corrected as shown below:

Column 1 line 1 "PACKAGEn" should read -- PACKAGE --.

Column 2 line 11 after "commercially" insert -- used for igniting --.

Signed and Sealed this

Fourteenth Day of July, 1992

Attest:

DOUGLAS B. COMER

Attesting Officer

Acting Commissioner of Patents and Trademarks